United States Patent [19]

Sokolich

[11] 4,251,686
[45] Feb. 17, 1981

[54] CLOSED SOUND DELIVERY SYSTEM

[76] Inventor: William G. Sokolich, 5309 Victoria Ave., Los Angeles, Calif. 90043

[21] Appl. No.: 965,482

[22] Filed: Dec. 1, 1978

[51] Int. Cl.³ .............................................. A61B 5/12
[52] U.S. Cl. .................................... 179/1 N; 73/585; 128/746; 179/107 E
[58] Field of Search ............... 179/1 N, 1 MN, 107 R, 179/107 E, 182 R; 128/746; 73/585, 589, 591

[56] References Cited

U.S. PATENT DOCUMENTS

| | | | |
|---|---|---|---|
| 3,294,193 | 12/1966 | Zwislocki | 179/1 N |
| 3,408,461 | 10/1968 | Langford | 179/107 E |
| 3,757,769 | 9/1973 | Arguimbau et al. | 179/1 N |
| 3,819,879 | 6/1974 | Baechtold | 179/182 |
| 3,882,848 | 5/1975 | Klar et al. | 179/1 N |
| 3,985,960 | 10/1976 | Wallace, Jr. | 179/107 E |
| 4,029,083 | 6/1977 | Baylor | 179/1 N |
| 4,057,051 | 11/1977 | Kerouac | 128/746 |
| 4,079,198 | 3/1978 | Bennett | 128/746 |

OTHER PUBLICATIONS

R. W. Leonard; "Probe-Tube Microphones", The Journal of the Acoustical Society of America, vol. 36, No. 10; Oct. 1964.
A. Barnebey, D. Nagel, E. Carterette; "An Earphone Coupling System for Acute Physiological Studies", The Journal of the Acoustical Society of America, vol. 52, No. 4, 1972; pp. 1256-1262.

*Primary Examiner*—Bernard Konick
*Assistant Examiner*—Randall P. Myers
*Attorney, Agent, or Firm*—Fraser and Bogucki

[57] ABSTRACT

A closed sound delivery system includes a sound generating unit coupled to provide sound to an ear in response to electrical input signals and an electrically equalized sound receiving unit coupled to accurately receive acoustical signals provided by the sound generating unit in the vicinity of an ear. The delivery system provides a pressure at the eardrum with a frequency response which remains flat up to about 30 KHz. The sound generating unit includes a low acoustical output impedance transducer and a suppressor element which attenuates acoustical energy emanating from all but a small central region of the transducer to minimize frequency response variations resulting from constructive and destructive interference of acoustical energy originating at different physical positions. The receiving unit has a 6 dB per octave high frequency roll off due to the characteristics of its terminating elements while an electrical high pass filter compensates for this roll off.

11 Claims, 3 Drawing Figures

CLOSED SOUND DELIVERY SYSTEM

BACKGROUND OF THE INVENTION

1. Field of the Invention

This invention relates to sound delivery systems for biological applications and particularly to a closed sound delivery system with a flat frequency response to 30 KHz.

2. Description of the Prior Art

This invention relates to the accurate generation and monitoring of sound at the eardrum. More specifically, this invention relates to the apparatus for minimizing linear distortions associated with coupling sound from an electro acoustic generator to the eardrum, as well as those associated with coupling sound at the eardrum to an electro acoustic receiver. By means of this invention, a time pattern of sound pressure which accurately resembles the time pattern of voltage applied to the electroacoustic generator is produced at the eardrum. Additionally, the time pattern of the output of electroacoustic receiver accurately resembles the time pattern of sound pressure at the eardrum.

Through investigations of relationships between measurable characteristics of acoustic stimuli and those of electrophysiological and behavioral responses, an increased understanding of the operation of the auditory system is achieved. The determination of these relationships depends upon the ability to both generate and monitor specific sound stimuli at a convenient location such as the eardrum. For example, studies employing speech or speech-like signals in which the time pattern of the acoustic waveform is of particular concern require a closed system for delivering and monitoring acoustic signals at the eardrum possessing the wide bandwidth with smooth and relatively flat response characteristics. Even in studies employing single frequency periodic signals, stimulus generation and specification is aided considerably by the use of such a system.

Considerable knowledge about the operation of the auditory system continues to be obtained from acute physiological experiments on small mammals. Sound systems used in these experiments vary widely in their design but generally contain three elements: (1) an earphone for generating sound; (2) a coupler consisting of air channels through which the sound travels between the earphone and the eardrum, and (3) a probe tube microphone used to monitor sound at the eardrum. Although the band-width of a given system is ultimately limited by that of the earphone used, the relative smoothness of the pressure response at the eardrum depends upon the acoustic properties of the earphone as well as those of the coupler, the ear, and the probe tube monitoring system. Accordingly, consideration of the acoustic properties of each of these elements and how they interact is required if specific performance criteria are to be achieved via a systematic design. Nonetheless, many current designs are based mainly on considerations of mechanical convenience. Consequently, acoustic performance is often marginally adequate and is generally achieved through a trial and error procedure which involves packing the air channels of both the coupler and the probe tube monitor with steel wool or nonabsorbent cotton. The end result of such practice is generally a compromise between sufficient bandwidth and sufficient smoothness of freuency response. It is possible to avoid this compromise by considering the acoustic properties of the individual elements of the system and by basing the design on fundamental principles of lumped-element and transmission line acoustics.

In A. R. Moller, "Acoustic Stimulator For Use in Acute Experiments On Cats", QPR No. 73, Res, Lab. Electron. MIT. (1964) pp. 181–185, there is disclosed a closed sound delivery system. The system includes a sound generator transducer connected through a cavity to a transmission tube and a receiver transducer connected to a transmission tube. Both tubes are filled with steel wool in order to flatten the system frequency response, resulting in altered response properties when either tube fills with blood. The frequency response of the receiver remains flat only to about 800 Hz and exhibits numerous resonant peaks and dips at higher frequencies. The use of a washer to decrease the air volume in front of the receiver transducer is indicated although its effect on high frequency response is not well documented. There is no suggestion of suppressing acoustical energy emanating from the periphery of the sound generator transducer in order to minimize frequency reponse deviations due to the effects of destructive and constructive interference.

In Alan Barnebey, David C. Nagel, and Edward C. Carterette, "An Earphone Coupling System for Acute Physiological Studies," *J. Acoust. Soc. Am.*, Vol. 52, Number 4, Part 2, pp. 1256–1262, 1972, there is disclosed an earphone system using a generally conical configuration to provide a gradual transition from a large diameter transducer to a small diameter transmission tube. Claim is made to a relatively flat frequency response from about 40 Hz to 10 KHz.

In J. P. Barton, J. K. Koester, and M. Mitchner, "Probe-tube Microphone for Pressure-Fluctuation Measurements in Harsh Environments," *J. Acoust. Soc. Am.*, Vol. 62, No. 5, pp. 1312–1314, 1977, it is suggested that an acoustical resistance be placed midway along the length of the transmission tube. A resultant reasonably flat frequency response approaching 10 KHz is claimed.

In Leo Beranek, *Acoustic Measurements*, John Wiley & Sons, New York (1949), pp. 186–189 and 730–735 there appears a discussion of a sound probe developed by R. H. Nichols (OSRD Report 4666, Electro-Acoustic Lab., Harvard University) which shows an attenuation of about 20 dB/octave above 100 Hz.

In W. West, "Probe Microphones as Laboratory Standards," *Acoustica*, Vol. 4 pp. 131–133, 1954, there is described an arrangement in which the transducer is disposed part way along a terminated transmission path.

R. W. Leonard, "Probe-tube Microphones," *J. Acoust. Soc. Am.*, Vol. 36, No. 10, pp. 1867–1871, 1964, reviews several different probe-tube microphone arrangements. However, the specific configuration in which the tube is terminated at its microphone end by a volume in series with an acoustic resistance is not described.

In W. West, "Probe Microphones as Laboratory Standards," *Acoustica* Vol. 4, pp. 131–133, 1954, various means of obtaining an approximate broad band resistive termination for probe microphones are described. However, because none of the configurations described provide high impedance at low frequencies they are not suitable for making accurate measurements in small volumes such as that presented by the ear at low frequencies.

David P. Egalf, "Mathematical Modeling of a Probe Tube Microphone," *J. Acoust. Soc. Am.*, Vol. 61, No. 1 pp. 200–205, 1977, discusses techniques for mathematical modeling of probe-tube microphones.

U.S. Pat. No. 3,985,960, "Stereophonic Sound Reproduction With Acoustically Matched Receiver Units Effecting Flat Frequency Response at Listener's Eardrums," Wallace, Jr., discloses a transducer which contacts an outer human ear. The frequency characteristics of the sound generating unit are selected to compensate for the characteristics of the human ear and the transducer itself. Unlike the present invention which relates to closed acoustical systems for biological applications this disclosure relates to entertainment systems and attempts to provide a flat frequency response to the eardrum notwithstanding distortions introduced by the passage of the acoustical signal through the sound generator and through the outer ear to the inner ear. No means of monitoring sound at the eardrum is provided. Additionally, it is not clear whether performance claims are based on real ear measurements or on those obtained from an ear simulator. The constant displacement, high acoustical output impedance, transducer feeds into a cavity which reduces the driving impedance and provide a flat frequency response pressure output. In contrast, the present invention uses a large diameter low output impedance transducer in conjunction with a suppressor element having a central aperture in which the resultant cavity is a byproduct of the geometrys of the suppressor element rather than an impedance reducing element.

Bell Laboratories, Memorandum For File, "A New Kind of Headphone Receiver," R. L. Wallace, Jr., Oct. 10, 1974, provides a disclosure which is similar to that of the patent.

An oral disclosure of the subject matter of this invention was made to the American Acoustical Society on Dec. 13, 1977 and an abstract of the disclosure was provided for review and approval by the Society in August or September 1977 and distributed to Society members on or about Nov. 22, 1977.

The above references are being included in the file history of the application for this patent for ease of access.

SUMMARY OF THE INVENTION

This invention provides a closed sound delivery system including a distortion free, flat frequency response sound generating unit capable of providing desired acoustical signals directly to the eardrum and a sound receiving unit disposed to detect acoustical signals actually appearing in the vicinity of the eardrum and provide an electrical output which accurately reflects the detected signals over a broad frequency range of at least 30 KHz. The sound generating unit includes a low acoustical output impedance, inexpensive transducer with a planar, circular vibrating diaphragm, a generally toroidal suppressor element, and a tube carrying the generated acoustical signal to a destination location such as an eardrum. The diameter of the sound generating unit tube is selected to provide an acoustical characteristic impedance which will minimize reflections of acoustic signals within the tube for a given application.

The sound receiving unit includes a transducer and a collar element defining a cavity connecting the transducer to a sound transmission tube. An end of the tube opposite the transducer extends to the sound destination point and may enter the sound transmission tube for the sound generating unit to terminate substantially concentrically and coterminously therewith. An acoustic resistance is placed in the receiver transmission tube at the cavity end thereof adjacent the transducer and matched to the tube's acoustic characteristic impedance to attenuate distributed transmission line resonances.

At lower frequencies the tube's transmission characteristics closely approximate a lumped inductive reactance while the cavity corresponds to a capacitive reactance. It is desirable to maintain the cavity small to maximize the frequency of resonance resulting from these reactances. However, at higher frequencies any mismatches in the transmission path and terminations cause resonant reflections to occur. The cavity must be sufficiently large to present an impedance that is much smaller than the acoustical resistance at the transducer end to permit attenuation of these distributed transmission line resonances. The cavity and acoustical resistance approximate a low pass filter with a roll off of 6 dB per octave above approximately 2.3 KHz.

The flat frequency response of the sound receiver unit is extended by providing an electrical filter at the output of the receiver transducer. The electrical filter has a constant low frequency attenuation which decreases at 6 dB per octave at higher frequencies to compensate and cancel the effect of the increasing high frequency attenuation produced by the acoustical filter. A low distortion, flat frequency response characteristic far surpassing prior arrangements is thus attained.

BRIEF DESCRIPTION OF THE DRAWINGS

A better understanding of this invention may be had from a consideration of the following detailed description taken in conjunction with the accompanying drawings in which.

DETAILED DESCRIPTION

Figure 1:
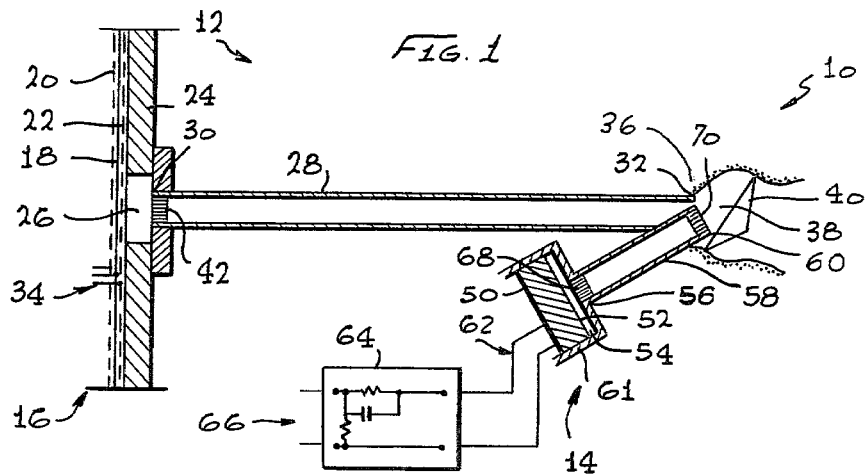
FIG. 1 is an idealized plan sectional view of a closed sound delivery system in accordance with the invention.

As shown in FIG. 1, a closed sound delivery system 10 in accordance with the invention includes a sound generating unit 12 and a sound receiving unit 14. The sound generating unit 12 includes a sending transducer 16 having a planar, circular diaphragm 18 disposed between electrostatic plates 20, 22. A toroidal suppressor element 24 is disposed adjacent the transducer 16 to suppress acoustical energy provided at peripheral regions thereof. A central, cylindrical aperture 26 in suppressor element 24 receives and passes therethrough an acoustical signal from transducer 16 to an air filled, hollow acoustical transmission tube 28, which may have an inside diameter of 3.56 mm and a length of 4 inches. Tube 28 has one end 30 adjacent transducer 16 and an opposite end 32. Conductors 34 provide an electrical signal to transducer 16 for conversion to a corresponding acoustical signal.

At the end 32 opposite transducer 16, tube 28 is adapted to engage the temporal bone 36 and substantially close an aperture therethrough leading through an air space 38 in front of the eardrum 40 of an animal such as a cat. An acoustical resistance 42 is disposed at transducer end 30 of tube 28.

The sound receiving unit 14 includes a receiver transducer 50 having a circular, planar diaphragm 52 which is acoustically coupled through a cavity 54 to one end 56 of an acoustical transmission tube 58, which may be a no. 17 hypodermic needle. An opposite end 60 of tube 58 may extend through the side wall of tube 28 near the end 32 thereof to terminate so as to receive acoustical signals occurring in the air space 38 in front of eardrum 40. A collar 61 extends about transducer 50 and defines cavity or volume 54.

Electrical wires 62 couple transducer 50 to an electrical filter 64 having electrical output wires 66 carrying a wide band electrical signal with a substantially flat frequency response characteristic from approximately 2 Hz to 30 KHz. Electrical filter 64 provides a low frequency attenuation which decreases at 6 dB per octave at higher frequencies to compensate for the 6 dB per octave high frequency attenuation provided by an acoustical filter resulting from cavity 54 and an acoustical termination resistance 68 disposed at end 56 of tube 58. An additional acoustical resistance 70 may be disposed at end 60 of tube 58.

Figure 2:
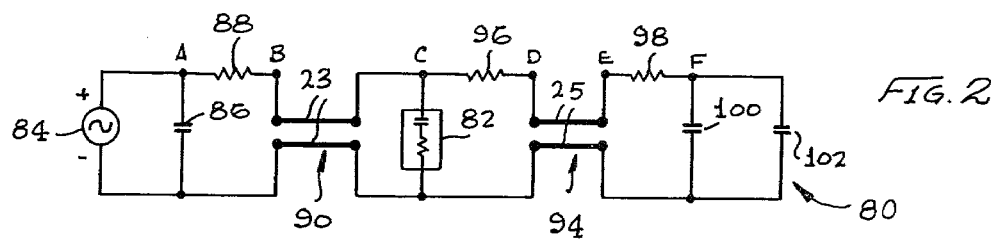
FIG. 2 is a schematic electrical equivalent circuit of the closed sound delivery system shown in FIG. 1.

FIGS. 1 and 2 illustrate a sound system and its electrical network equivalent which is in accordance with a typical embodiment of this invention. Transducer 16 of the sound source 12 is a low acoustic output impedance electrostatic transducer which converts the electrical signal supplied via wires 34 into an acoustic output signal. In one embodiment of the invention, the transducer 16 is a SRX MK III push-pull electrostatic ear-speaker which is widely used in a Stax high fidelity headset. It should be noted, however, that a variety of transducer elements can be employed. Transducer 16 is retained within a rigid structure which, for convenience, is not shown, and radiates sound from both sides of diaphragm 18. Sound from the side of diaphragm 18 not facing eardrum 40 can radiate into either an open or a closed space. Sound from the side of diaphragm 18 facing the eardrum 40 is collected in volume 26 which is formed primarily by suppressor element 24. Suppressor element 24, in conjunction with transducer 16, establishes a smooth, relatively flat and extended pressure response at end 30 of tube 28 by attenuating sound radiating from the periphery of diaphragm 18 facing eardrum 40. This avoids peaks and dips in the frequency response due to reinforcement and cancellation of sound waves which travel different distances. Acoustic resistance 42 is mounted at the end 30 of tube 28 at its junctions with volume 26. Acoustic resistance 42 may be any material exhibiting the desired acoustic resistance. Many materials which exhibit an acoustic resistance are known in the art. One such material which has been found to be suitable for the practice of this invention is an electro-formed mesh manufactured by Buckbee Mears Company. Sound flowing through resistance 42 propagates down tube 28 to the eardrum 40 where it is sampled by probe tube 58. Probe tube 58 uses air as a transmissive medium and can be either open or can contain resistance 70 across its end 60 nearest the eardrum 40. Sound entering probe tube 58 travels to resistance 68 and into volume 54 which includes receiver transducer 50 as a wall. Receiver transducer 50 is a small electroacoustic transducer element which converts the acoustic signal in volume 54 to an electrical signal which can be monitored via wires 62. For convenience, the supporting structure associated with the probe tube 58, acoustic resistance element 68, and receiver transducer 50 is not shown. In one embodiment, receiver transducer 50 is a Bruel and Kjaer 4134 precision condenser microphone which is widely used for acoustic measurements. It should be noted however that a variety of receiver elements can be employed. Furthermore, it should be noted that acoustic resistances 68 and 70 may be any material exhibiting the desired resistance when mounted at the ends 56 and 60 of probe tube 58.

FIG. 2 shows an electrical network 80 which is an electrical analog of the sound delivery and monitoring system described in FIG. 1. As shown in FIG. 2, the portion of the circuit to the left of node C represents the sound delivery portion 12 of the system 10, whereas that to the right of node C represents the sound monitor part 14 of the system. Element 82 between node C and ground represents the impedance at the eardrum 40. The electrical equivalent of the impedance at the eardrum 40 of a cat is shon by way of simplified example as a series combination of a capacitor and a resistor. In the embodiment shown, motor transducer 16 and suppressor element 24 produce a smooth relatively flat and extended pressure response in volume 26 and are represented as an analog voltage source 84 in the circuit. Volume 26 has as its electrical analog capacitor 86. It is important to realize that volume 26 does not significantly alter the impedance of transducer 16, but is instead merely a byproduct of the geometry of suppressor element 24 which, in conjunction with transducer 16 serves to produce a substantially frequency independent pressure at the volume side of resistance 42. Resistor 88 connected between nodes A and B is the electrical analog of acoustic resistance 42 which serves to increase the impedance seen by delivery tube 28 as represented by electrical transmission line 90. Acoustic resistance 42 is constructed such that the electrical resistance of resistor 88 is approximately equal to the characteristic impedance 23 of the delivery tube 28 and accordingly minimizes wave reflections from the transducer end of the tube 28. The characteristic impedance 23 of tube 28 is selected so as to minimize wave reflections from the eardrum end 32 of the tube 28. Probe tube 58 has as its electrical analog electrical trnsmission line 94 having characteristic impedance 25. Resistances 96 and 98 are the electrical analogs of acoustic resistances 70 and 68 respectively. It is important to recognize that resistance 70 is not essential for proper operation of the probe tube monitor 14. Those skilled in the art will recognize that resistance 70 essentially serves to increase the input resistance of the monitor system 14 at the expense of sensitivity. On the other hand, resistance 68 serves to minimize wave reflections from the receiver end 56 of the probe tube 58 and theoretically should have a value equal to the characteristic impedance of the tube 58. Those skilled in the art will also recognize that volume 54 having an electrical analog of capacitance 100 must be sufficiently large that the magnitude of its reactance is small compared to resistance 98 at the lowest distributed resonance of tube 58. The reactance of volume 54 and transducer 50 in conjunction with acoustic resistance 68 corresponding to electrical analogs 100, 102 and 98 respectively produce a 6 dB per octave roll off at frequencies above a lumped element resonance point produced by the reactance of volume 54 and receiver element 50 in conjunction with the reactance of the air mass in tube 58. It is desirable to have volume 54 as small as possible in order to extend the flat portion of the low frequency response as high as possible while still maintaining the volume sufficiently large that its reactance is small compared to the terminating resistance 98 at the frequency of the first distributed transmission line resonance of tube 58. The size of volume 54 should also be influenced by mechanical constraints such as required tube length and maximum diameter. Since the input impedance of the probe system is in parallel with that of the eardrum, it is advantageous that the magnitude of the former be much greater than that of the latter so that loading effects by the monitor need not be a major consideration in the design of the delivery system 10. Capacitor 102 represents to a first order of approximation, the acoustic behavior of the transducer 50 in one embodiment of the invention.

Figure 3:
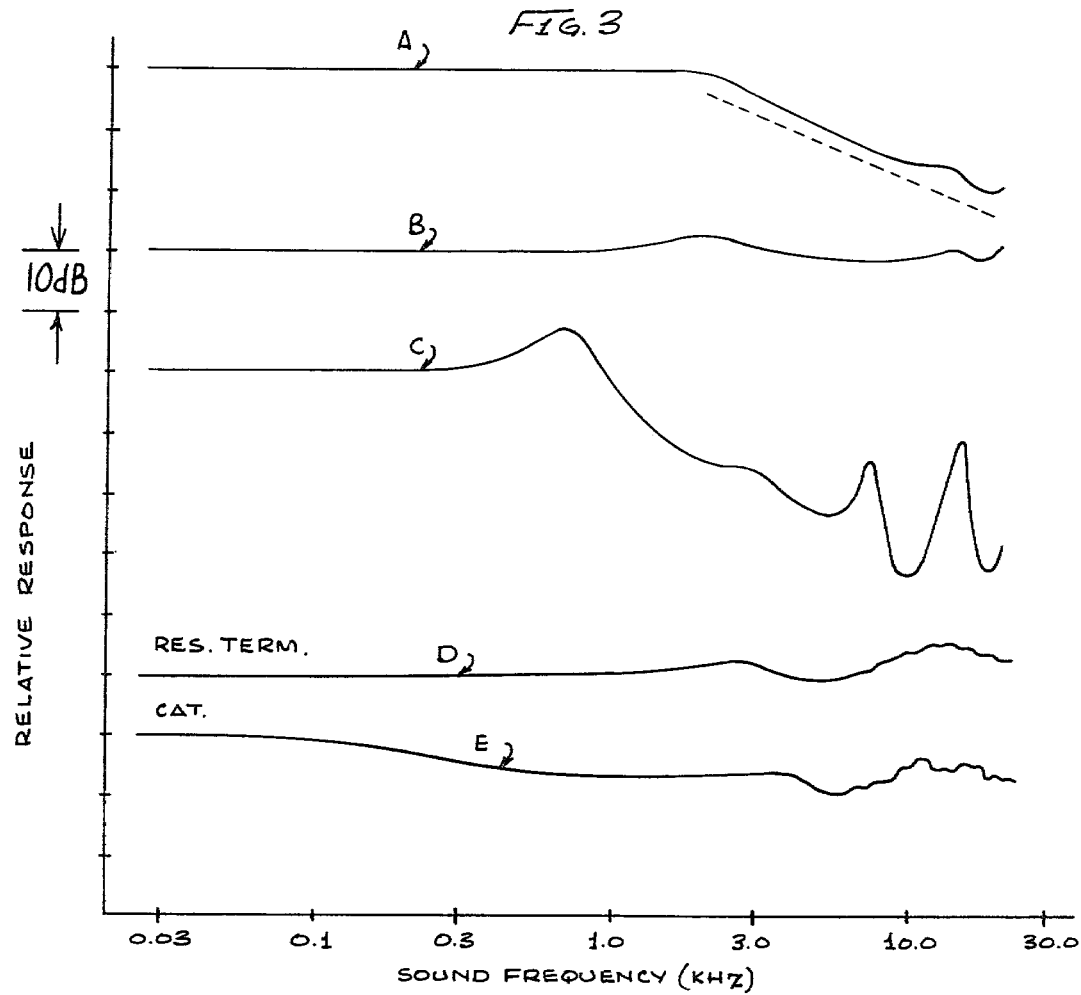
FIG. 3 is a graphical representation of several frequency characteristics which are helpful in understanding the closed sound delivery system shown in FIG. 1.

FIG. 3 shows the frequency response of a probe tube monitor constructed in accordance with the typical embodiment of this invention that is illustrated in FIG. 1. The data shown are the electrical output of the receiver element for constant sound pressure at the entrance of the probe tube. Whereas Curve A shows the unequalized response, Curve B shows the response after external electrical equalization of 6 dB/octave is provided above approximately 2.3 KHz by filter 64. By contrast, Curve C shows the response of a typical conventional prior art probe tube monitor. It should be noted that the equalized response is substantially flat to 30 KHz, although not specifically shown because of limitations of the automatic equipment used to plot the data.

FIG. 3 also shows the frequency response of the sound delivery portion 12 of the system 10 as measured using monitor 14 just described. Shown is the output of the receiving unit 14 equalized by filter 64 for constant voltage applied to the transducer 16 of the delivery portion 12 of the system 10. Curve D shows the response when the sound delivery tube 28 is terminated acoustically in its characteristic impedance. Curve E shows a typical response when the delivery tube 28 is terminated by the eardrum of a live cat. The low frequency plateau in the curve E is an inherent property of the embodiment described and can be eliminated if desired by either simple low frequency electrical equalization of the driving voltage or by implementing the acoustic equivalent of an inductance and resistance in series to ground anywhere between nodes B and F. It should be noted that the response extends smoothly to 30 KHz, although not directly shown. It should also be noted that to obtain the actual responses it is necessary to correct those shown in curves D and E by the monitor calibration of Curve B. Under most conditions however, this correction is negligible and need be applied only in the most exacting applications.

In one example suppressor element 24 has an outside diameter of 1.72 inch, an inside diameter of 0.5 inch and a longitudinally extending thickness of 0.091 inch. The volume of cavity 26 occupies 0.3 cc corresponding to a capacitance 86 of 0.2 $\mu f$. Transmission tube 28 has an inside diameter of 3.56 mm corresponding to a characteristic impedance of 410 ohms and acoustical resistance 42 corresponds to a resistor 88 of 405 ohms. Below approximately 1 KHz the impedance at the eardrum has a large reactive component which causes wave reflections at the driving frequency. In order to avoid resonances which destroy the flat frequency response at these lower frequencies tube 28 should be shorter than one-fourth wave length at a frequency of 1 KHz and below. If tube 28 is longer than 4 inches the frequency of the distributed transmission line reflective resonances becomes undesirably low.

Collar 61 has an inside diameter of 0.485 inch and cavity 54 provides a volume of 0.02 cc. The transducer 50 provides a further equivalent volume of about 0.01 cc for a total equivalent volume of about 0.30 cc. The corresponding capacitors 100 and 102 are about 0.014 $\mu f$ and 0.007 $\mu f$. Transmission tube 58 has an outside diameter of 1.5 mm and an inside diameter of 1 mm, providing an acoustical characteristic impedance of 5.3 K (cgs). Acoustical resistance 68 corresponding to resistor 98 has a value of 5.1 K. Acoustical resistance 70 corresponding to resistance 96 if 0 for maximum high frequency sensitivity, but may be non-zero if a higher input impedance is required for a specific application.

While a particular arrangement of a closed sound delivery system in accordance with the invention has been shown and described for the purpose of enabling a person of ordinary skill in the art to make and use the invention, it should be appreciated that the invention is not limited thereto. Accordingly, any modifications, variations or equivalent arrangements within the scope of the attached claims should be considered to be within the scope of the invention.

What is claimed is:

1. A closed sound delivery system comprising:
   a sound generating unit including a low acoustical output impedance first transducer having a diaphragm providing as a transducer output an acoustical signal corresponding to an input electrical signal, a suppressor element disposed in close proximity to the diaphragm to attenuate acoustical energy generated by the transducer radially outward of a central region of the diaphragm and having a central aperture in opposed relation to the central region of the diaphragm which receives and passes acoustical signals generated by the transducer, and a first tubular element having one end connected to receive acoustical signals from the transducer through the central aperture and an opposite end adapted for engagement within an ear; and
   a sound receiving unit including a second transducer coupled to receive acoustical signals generated by the first transducer and provide an electrical signal indicative thereof and a second tubular element having one end coupled to provide acoustical signals to the second transducer and an opposite end adapted to receive acoustical signals from the opposite end of the first tubular element.

2. The sound delivery system according to claim 1 above, further comprising an acoustic resistance disposed at the one end of the second tubular element and having a magnitude substantially equal to the acoustical characteristic impedance of the second tubular element.

3. The sound delivery system according to claim 1 or claim 2 above, wherein the opposite ends of the first and second tubular elements are positioned adjacent the temporal bone in close proximity to the ear drum with no substantial portion of an ear canal between said opposite ends and the ear drum; wherein the transmissive medium of the first tubular element is air and wherein the acoustical characteristic impedance of the first tubular element matches the impedance occurring adjacent the ear drum at the opposite end of the first tubular element.

4. The sound delivery system according to claim 3 above, wherein the first tubular element has an inside diameter of approximately 3.56 mm and a characteristic impedance of approximately 410 ohms (cgs) and wherein the second tubular element has an inside diameter of approximately 1 mm and a characteristic impedance of approximately 5.3 K (cgs).

5. The sound delivery system according to claim 3 above, further comprising a second acoustical resistance disposed at the first end of the first tubular element which matches the acoustical characteristic impedance of the first tubular element and a third acoustical resistance disposed at the opposite end of the second tubular element.

6. The sound delivery system according to claim 2 above, further comprising means defining a cavity coupling the one end of the second tubular element to the second transducer, the cavity providing an acoustical impedance which is much smaller than the acoustical resistance at the frequency of the first distributed transmission line resonance of the second tubular element and a high pass electrical filter connected to the electrical output of the second transducer, the electrical filter having parameters selected to compensate for a 6 dB per octave high frequency attenuation provided by the acoustical resistor and cavity to provide a substantially flat frequency response at the output of the electrical filter from approximately 2 Hz to 30 KHz.

7. A sound generating unit comprising:
a transducer having a diaphragm and being coupled to receive an electrical signal as an input and generate an acoustical signal corresponding to the input as an output;
a suppressor element disposed in opposed relation to the diaphragm as close thereto as possible without interference with the operation of the diaphragm, the suppressor element having a central aperture extending therethrough and being operable to attenuate acoustical energy emanating from the periphery of the diaphragm while passing acoustical energy emanating from a region of the diaphragm opposite the central aperture; and
a hollow tube adapted to connect the central aperture of the suppressor element to an ear.

8. The sound generating unit according to claim 7 above, wherein the cross-sectional area of the space inside the tube is less than the cross-sectional area of the central aperture.

9. The sound generating unit according to claim 8 above, wherein an end of the tube opposite the end coupled to the central aperture engages with temporal bone surrounding an ear drum at an aperture therethrough in close proximity to the ear drum for providing acoustical communication between said opposite end and an ear drum.

10. A sound receiving unit comprising:
a transducer coupled to receive an acoustical signal as an input and generate as an output an electrical signal corresponding to the input signal;
a hollow tube having an acoustical characteristic impedance between one end coupled to the transducer and an opposite end adapted to receive an acoustical signal appearing in the vicinity of an ear drum;
an acoustical resistance matching an acoustical impedance of the tube disposed at the one end of the tube; and
an element defining a cavity connecting the one end of the tube to the transducer, the cavity having a volume sufficiently small to provide an acoustical lumped-element resonance in combination with the tube at as high a frequency as possible while being sufficiently large to cause the acoustical impedance thereof to be much smaller than the acoustical resistance at the frequency of the first distributed transmission line resonance of the tube.

11. The sound receiving unit according to claim 10 above, further comprising a high pass electrical filter coupled to the output of the transducer to provide a substantially flat frequency response from approximately 2 Hz to a frequency greater than the frequency of the first distributed transmission line resonance of the tube.

* * * * *